US00PP33183P2

(12) United States Plant Patent
Adams et al.

(10) Patent No.: US PP33,183 P2
(45) Date of Patent: Jun. 22, 2021

(54) HEMP PLANT NAMED 'C2B'

(50) Latin Name: ***Cannabis* spp.**
Varietal Denomination: C2B

(71) Applicant: GeneticsCubed, LLC, Hurricane, UT (US)

(72) Inventors: Arthur Adams, Santa Clara, CA (US); Thomas Azwell, Berkeley, CA (US); Chloe Ciotti, Berkeley, CA (US)

( * ) Notice: Subject to any disclaimer, the term of this patent is extended or adjusted under 35 U.S.C. 154(b) by 0 days.

(21) Appl. No.: 16/873,477

(22) Filed: Apr. 17, 2020

(51) Int. Cl.
*A01H 5/02* (2018.01)
*A01H 6/28* (2018.01)

(52) U.S. Cl.
USPC ..... Plt./258

(58) Field of Classification Search
USPC ..... Plt./258, 263.1
CPC ... A01H 5/02; A01H 5/00; A01H 5/12; A01H 6/28; A61K 36/185
See application file for complete search history.

*Primary Examiner* — June Hwu
(74) *Attorney, Agent, or Firm* — David R. Conklin; Kirton McConkie

(57) ABSTRACT

The present invention provides a new and distinct variety of hemp designated as 'C2B', wherein 'C2B' comprises a cannabidiol:cannabichromene:tetryhydrocannabinol ratio of 25:9:1 which is 4-8 times greater than the average amount of cannabichromene found in other *Cannabis* varieties.

7 Drawing Sheets

Latin name of the genus and species of the plant claimed: *Cannabis* spp.

Variety denomination: 'C2B'.

BACKGROUND OF THE INVENTION

*Cannabis* is the genus of a variety of species—*Cannabis sativa, Cannabis ruderalis,* and *Cannabis indica*—which is often used as an umbrella term to refer to them all. This misclassification of the different species has made it difficult to properly distinguish between and understand the best ways to utilize the different varieties of these plants.

According to the 2018 Farm Bill, Hemp is a variety of *Cannabis sativa* that is distinguished by its low tetrahydrocannabinol (THC) levels of less than 0.3%. THC is the only currently known psychoactive compound found in *Cannabis*, however there are many additional cannabinoid compounds that can be utilized in a variety of ways. The exact concentration results based on lab testing of dried flowers will vary depending on growing conditions of the plant, and sampling, preparation, and testing methods used. THC production, for example, is a natural defense mechanism for the plant, meaning in high stress or threatening environments the specific plant will produce higher levels of THC. Because of this inconsistency, many state labs are allowing slightly higher levels of THC in the tests as anything under 1% THC has not been proven to have psychoactive effects.

For the purpose of this study on 'C2B', the cannabinoid percentages are recorded based on a plant grown in a high-stress environment to determine the maximum concentration of THC that will be produced by this specific strain. The results conclude that the 'C2B' is a type-III hemp cultivar meaning it does not possess the allele to ever make more than 0.5% THC (and thus is not suitable for marijuana use). Additionally, 'C2B' is a new, unique variety because of its composition of other cannabinoids, terpenes, and flavonoids. Unlike many other *Cannabis* varieties, 'C2B' has a 25:9:1 cannabidiol:cannabichromene:tetrahydrocannabinol (CBD:CBC:THC) ratio which has not been identified thus far in other strains. Therefore, 'C2B' can be used to extract CBD and CBC for medicinal applications.

With the recent legalization of hemp in 2018, the studies on medicinal effects of CBD are only at the beginning. CBD has been proven to alleviate nausea, chronic pain, and spasticity due to MS, to reduce blood pressure, to work as an anticonvulsant, antipsychotic, and anti-inflammatory and so much more. CBC, on the other hand, has only been isolated in such small concentrations that extensive research is required to continue understanding the possibilities for this compound. So far, CBC has been shown to act as an antidepressant and anti-inflammatory, is used to treat acne and hypermotility, and is rumored to kill cancer cells.

'C2B' was developed in a selective breeding program by performing controlled fertilization of known, high-performing hemp varieties. It was created by breeding both *Cannabis sativa* and *Cannabis indica* species together to create this unique hybrid. The purpose of the research was to determine what methods would allow for low THC levels in stressful, less-than-ideal environmental conditions (e.g., low-pH soil, high-salinity soil, dry environments, short growing seasons, etc.). The research also was striving to isolate varieties of plants with high concentrations of cannabinoids that have not been isolated in mass. 'C2B' was the best-performing individual selected from 200 seed phenotypes with CBC levels nearly four to eight times the industry average. Most *Cannabis* varieties have no detectable level of CBC, and none of the other plants of the 200 seed phenotypes exhibited more than 50% of the 'C2B' CBC levels.

BRIEF SUMMARY OF THE INVENTION

This invention relates to a new and distinctive hemp cultivar designated as 'C2B', wherein 'C2B' comprises a cannabidiol:cannabichromene:tetrahydrocannabinol ratio of 25:9:1 which is 4-8 times the average amount of cannabichromene found in other *Cannabis* varieties.

As used herein, the term "cultivar" is used interchangeably with the terms "variety," strain," and/or "clone."

Progenies have been reproduced asexually via apical stem cuttings from vegetative plants.

BRIEF DESCRIPTION OF THE DRAWINGS

The accompanying photographs illustrate the new hemp variety.

DETAILED BOTANICAL DESCRIPTION

Figure 1:
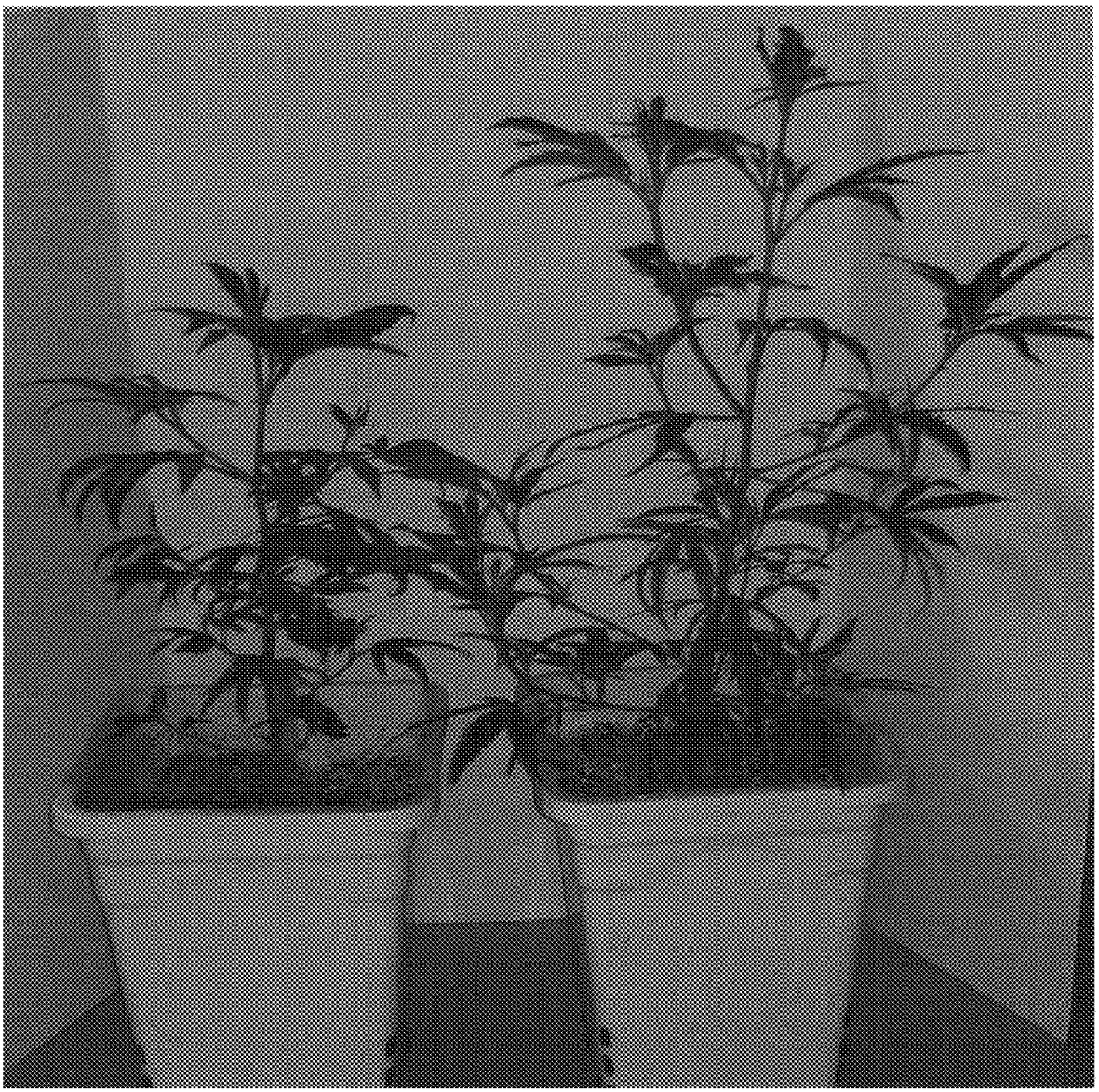
FIG. 1 shows a perspective view of a CC mother on the left next to a 'C2B' on the right, both grown from clones and planted in soil at the same time, at 23 days from the time the clones were planted in soil.
Figure 2:
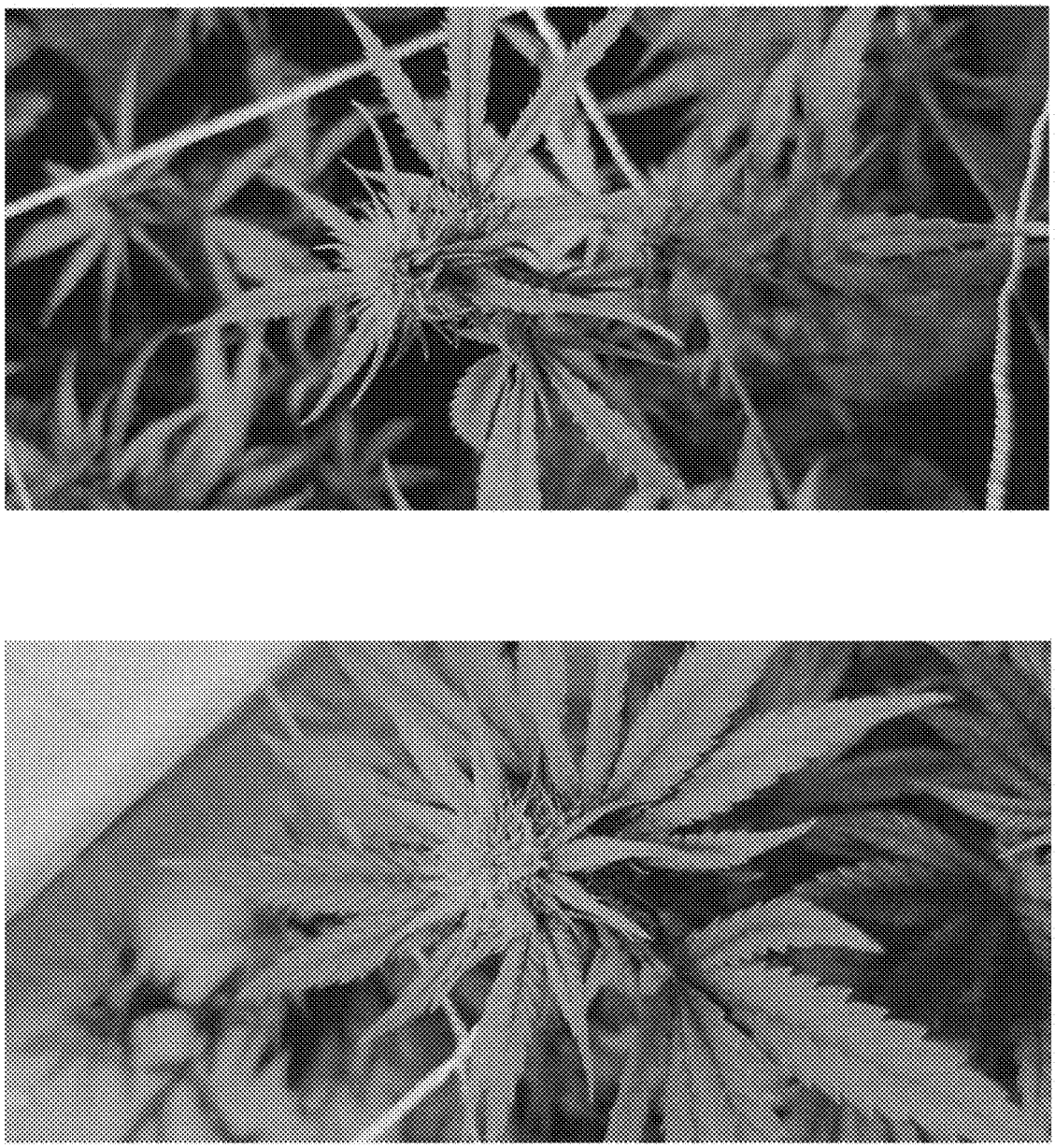
FIG. 2 shows top views of apical buds of a CC mother on the left and of a 'C2B' on the right, at 21 days after the flowering cycle was introduced.
Figure 3:
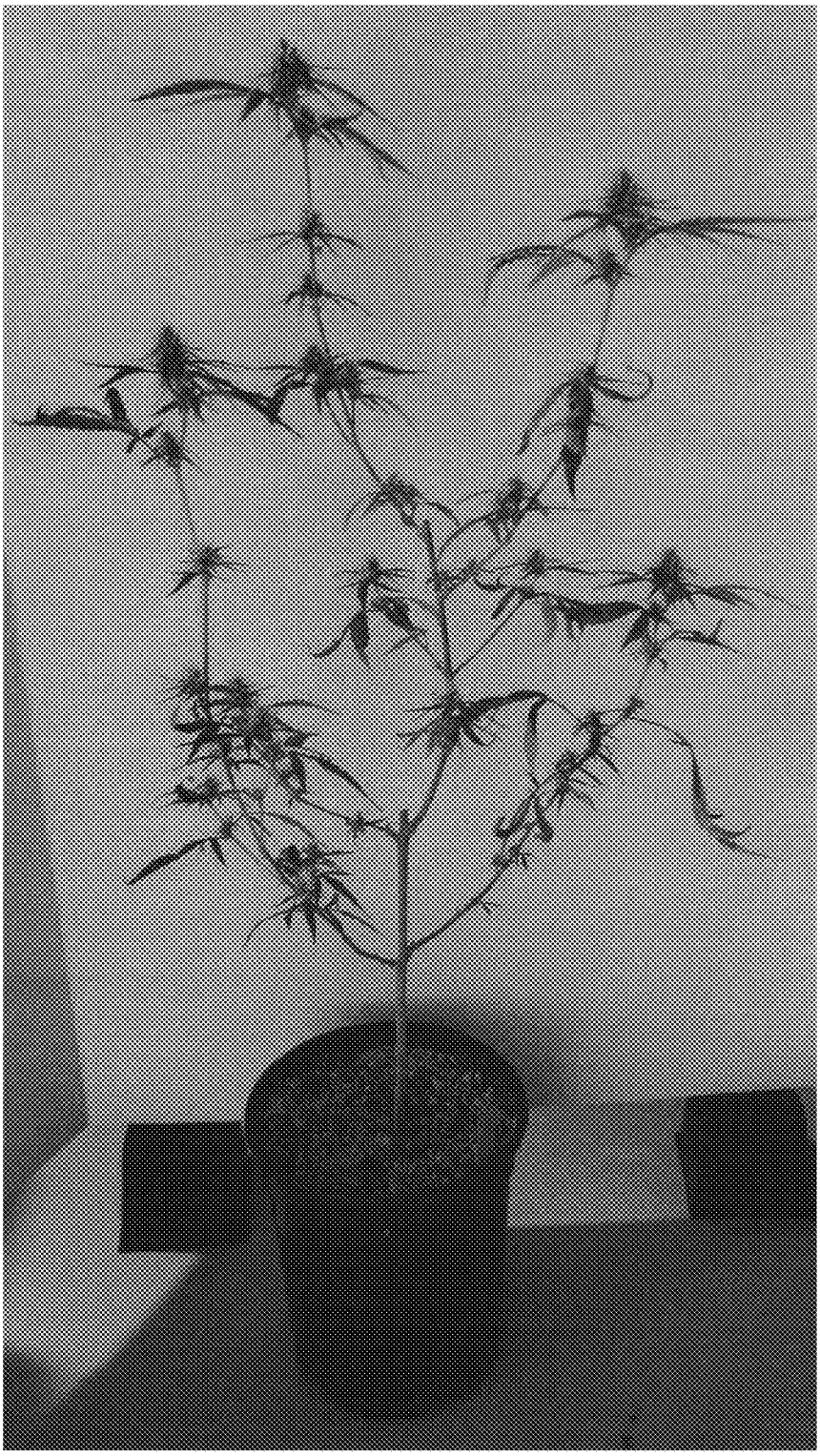
FIG. 3 shows a perspective view of a defoliated 'C2B' plant on day 26 of the flowering cycle (due to defoliation, branching is not natural)
Figure 4:
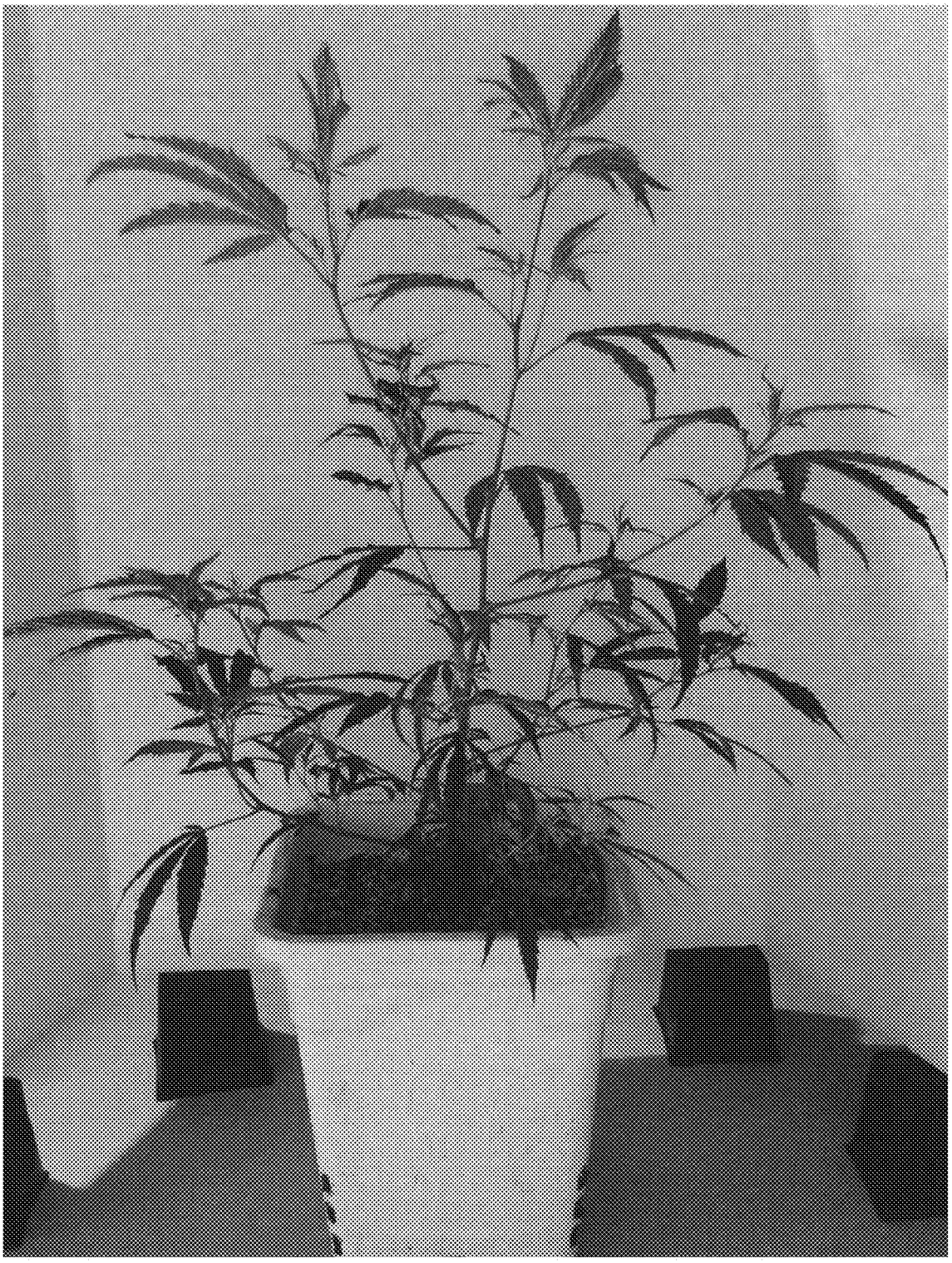
FIG. 4 shows a perspective view of a 'C2B' plant on day 25 after the rockwool clone was planted in soil, grown in 24-hour light with no defoliation or manipulation other than initially being planted in a 3-inch pot then being transplanted to a 3-gallon pot.
Figure 5:
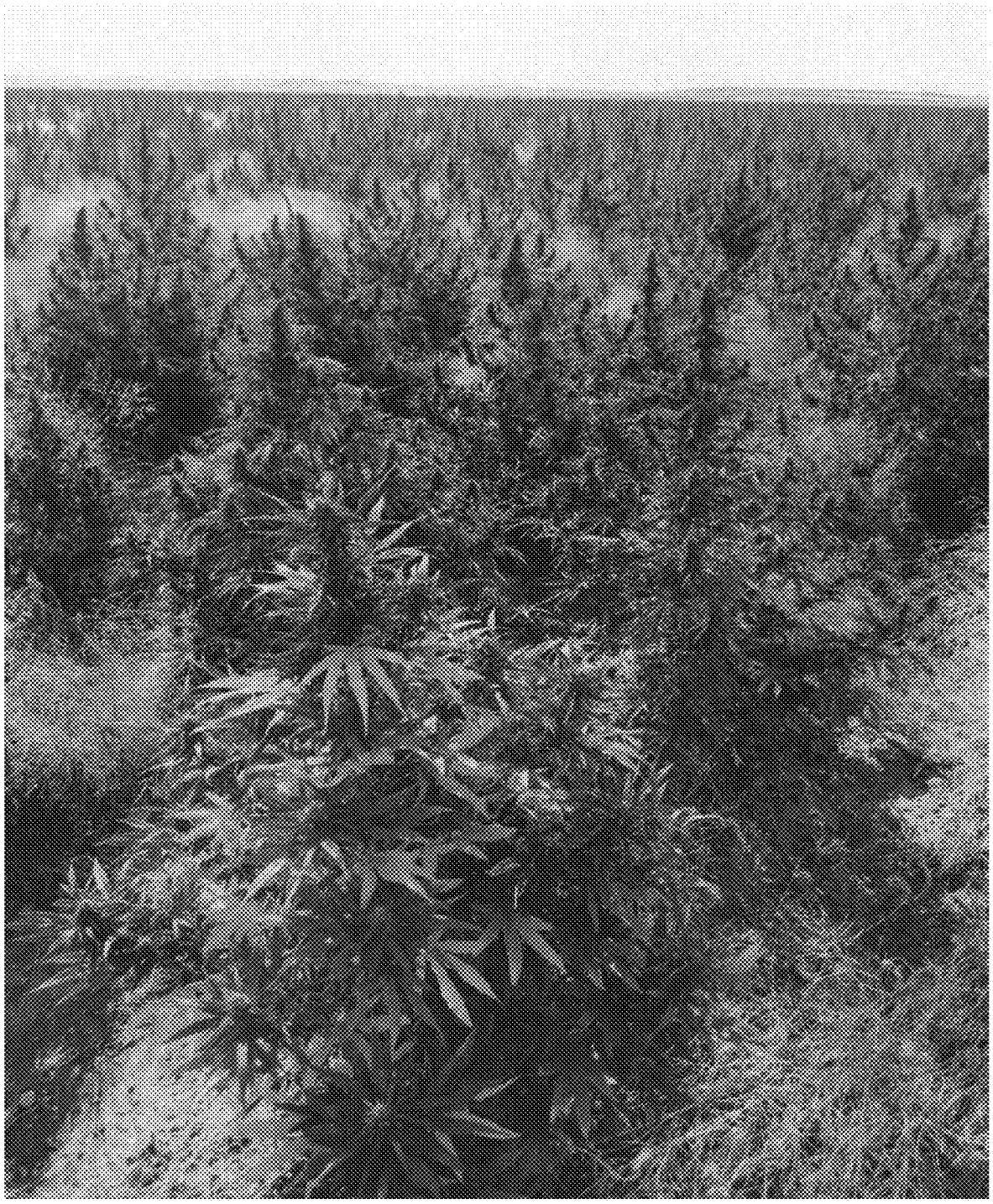
FIG. 5 shows a perspective view of 'C2B' taken two weeks prior to harvest.

'C2B' has been examined in manipulated conditions grown indoors in Black Point, Calif. The variety has not been grown in all possible conditions, thus different environmental factors alter the appearance or composition of this phenotype. The individual has been reproduced asexually via apical stem cuttings from vegetative plants and remains stable and reproduces true to type in successive generations of asexual reproduction.

In the following description, the color determination is in accordance with The Royal Horticultural Society Colour Charts, Fifth Edition, except where general color terms of ordinary dictionary significance are used.

TABLE I

| General | |
|---|---|
| Characteristics | New Variety |
| Plant Life Form | Herbaceous plant (herb) |
| Plant Growth Habit | Upright, dioecious, annual, no hermaphrodite, or monoecious, tendencies without stress conditions. |
| Plant origin | 'C2B' was created in a selective breeding program from a cross between the Mother, CC, hemp variety and the Father, K, hemp variety. |
| Plant Propagation | Asexually reproduced via apical stem cutting and cloning from mother in vegetative state. |
| Propagation ease | Easy |
| Propagation Condition | 80° F., 90% humidity |
| Height (unit: feet) | Outdoors may reach 15-17 feet at maturity. Indoors may reach 3-6 feet at maturity depending on growth conditions. |

TABLE I-continued

| General | |
|---|---|
| Width (unit: feet) | Outdoors may reach 10 feet at maturity. Indoors may reach 1-2 feet depending on growth conditions. This plant is more slender than typical *Cannabis* plants having less foliage and large internodes. |
| Time to Harvest | 75 Days from Induction of flowering light cycle |
| Resistance to Pests or disease | Exhibits resistance to *Podosphaera macularis* (Powdery Mildew) and *Botrytis cinerea* (Grey Mold Fungus). Has resistance to *Phorodon cannabis* (Bhang Aphid), *Myzus persicae* (Green Peach Aphid), Aphis fabae (Black Bean Aphid), *Tetranychu surticae* (Two-Spotted Spider Mite) and *Panonychus ulmi* (Red Spider Mite). |
| Genetically Modified Organism? | No |
| Characteristics | Parental Variety (CC) (Female Plant) |
| Plant Life Form | Herbaceous plant (herb) |
| Plant Growth Habit | Upright, dioecious, annual, no hermaphrodite or monoecious tendencies without stress conditions. |
| Plant origin | Origin unknown |
| Plant Propagation | Asexually reproduced via apical stem cutting and cloning from CC in vegetative state. |
| Propagation ease | Easy |
| Propagation Condition | 80° F., 90% humidity |
| Height (unit: feet) | Outdoors may reach 8-10 feet at maturity. Indoors may reach 3-4 feet depending on growth conditions. |
| Width (unit: feet) | Outdoors may reach 6-8 feet. Indoors may reach 1-2 feet. |
| Time to Harvest | 60 Days from Induction of flowering light cycle |
| Resistance to Pests or disease | More-prone to Podosphaera macularis (Powdery Mildew) than 'C2B'. Has resistance to *Phorodon cannabis* (Bhang Aphid), *Myzus persicae* (Green Peach Aphid), *Aphis fabae* (Black Bean Aphid) and *Tetranychus urticae* (Two-Spotted Spider Mite and Red Spider Mite). |
| Genetically Modified Organism? | No |

TABLE II

| Leaf/Foliage | |
|---|---|
| Characteristics | New Variety |
| Leaf Arrangement | Spiral alternate leaf arrangement when grown from a cutting. Stem is less angled between nodes as compared to mother. |
| Leaf Shape | Palmately compound with 3-5 leaflets in mature growth. |
| Leaf Structure | Sharply serrated margins. Skinny oval to lanceolate leaflets, sometimes appear falcate. Apex and base are acuminate, apex longer tapering. More narrow leaf |
| Leaf Margins | Serrate margins. Outer side of the serration is concave to straight. Inner side is convex. Tip of each serration slightly curls. |
| Leaf Hairs | Absent |
| Leaf Length with Petiole at Maturity | 15-22 cm |

TABLE II-continued

| Leaf/Foliage | |
|---|---|
| Petiole Length at Maturity | 4-8 cm |
| Petiole Color (RHS Number) | 149B to 150A |
| Anthocyanin color and intensity in Petioles | Green but may show light lavender |
| Stipule length at maturity | 1-4 mm |
| Stipule shape | Very small, lance shape. Broad/rounded base with acuminate/long tapering apex. |
| Stipule Color (RHS Number) | 149B to 150A |
| Number of Leaflets | 3-5 throughout life cycle |
| Middle Largest (longest leaflet) length | 8-15 cm |
| Middle Largest (longest leaflet) width | 1.1-2.3 cm |
| Middle Largest (longest Leaflet) length/width Ratio | About 7:1 |
| Number of teeth of middle leaflet | 28-32 |
| Leaf (upper side) color (RHS Number) | 141A and 134A |
| Leaf (lower side) color (RHS Number) | 144A-B |
| Leaf Glossiness | Not very. More matte, slight gloss reflection but not shiny, |
| Vein/midrib shape | Midveins branch palmately with the leaflets, 2° veins are pinnate and branch towards the apex of the serrations, they are relatively straight until they near the margins and they may angle upwards slightly. 3° veins are palmate slightly branching from 2° veins. 3° veins close to the margin will branch to the dip between serrations. Only 1° and 2° veins are visible from the top of the leaf |
| Vein/midrib color (RHS Number) | 149B-C |
| Aroma | Flower has an earth aroma with a hint of berry wine and pepper. |

| Characteristics | Parental Variety (CC) (Female Plant) |
|---|---|
| Leaf Arrangement | Spirally alternate when grown from a cutting. Stalk alternates directions back and forth between branches. |
| Leaf Shape | Palmately compound with 5-7 leaflets throughout the life cycle. |
| Leaf Structure | Serrated margins. Elliptical leaf with tapering base and apex. Middle section of leaflets are wide. |
| Leaf Margins | Evenly serrated. Point of serration is more acuminate/tapering to a point. Inner and outer sides of serrations are convex. |
| Leaf Hairs | None |
| Leaf Length with Petiole at Maturity | 13.1-19 cm |
| Petiole Length at Maturity | 3-5.5 cm |
| Petiole Color (RHS Number) | 150A |
| Anthocyanin color and intensity in Petioles | Purple to green |

TABLE II-continued

| Leaf/Foliage | |
|---|---|
| Stipule length at maturity | 1.5-3 mm |
| Stipule shape | Very small, lance shape. Broad/rounded base with acuminate/long tapering apex. |
| Stipule Color (RHS Number) | 150A |
| Number of Leaflets | 5-7 throughout life cycle |
| Middle Largest (longest leaflet) length | 9.3-13 cm |
| Middle Largest (longest leaflet) width | 2-4 cm |
| Middle Largest (longest Leaflet) length/width Ratio | About 4:1 |
| Number of teeth of middle leaflet | 23-25 |
| Leaf (upper side) color (RHS Number) | N144C |
| Leaf (lower side) color (RHS Number) | 149A |
| Leaf Glossiness | Bottom is matte, top has slight light reflection but not shiny |
| Vein/midrib shape | Midvein is palmate with leaflets. 2° veins are pinnate and straight. 3° veins are also palmate and branch from 10 and 2° veins. All three types of veins are slightly visible from the top. |
| Vein/midrib color (RHS Number) | 149C |
| Aroma | Flower has a spicy pepper with a sweet floral fragrance. |

TABLE III

Figure 6:
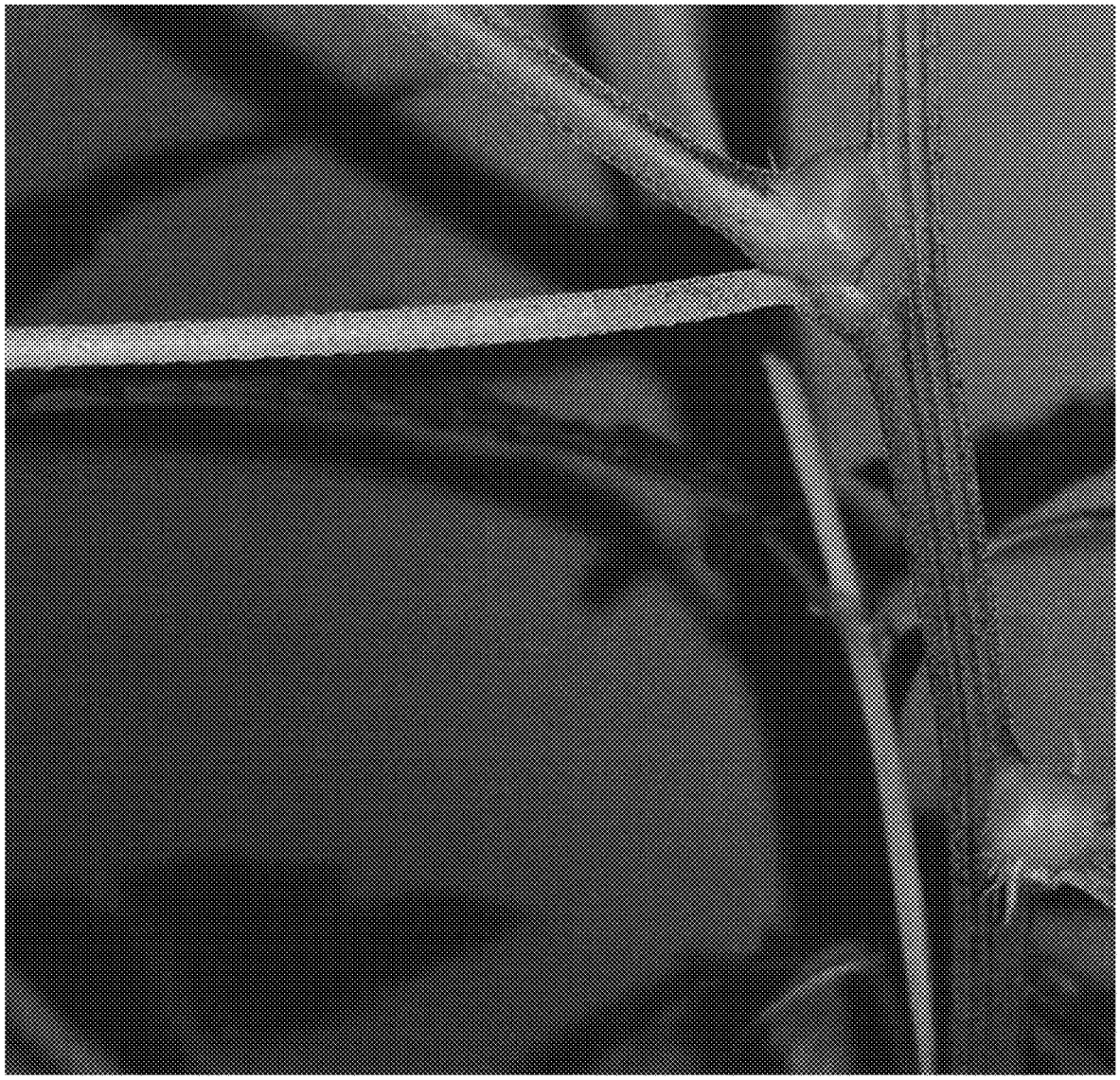
FIG. 6 shows a close-up perspective view of 'C2B' stem, illustrating stem shape.
Figure 7:
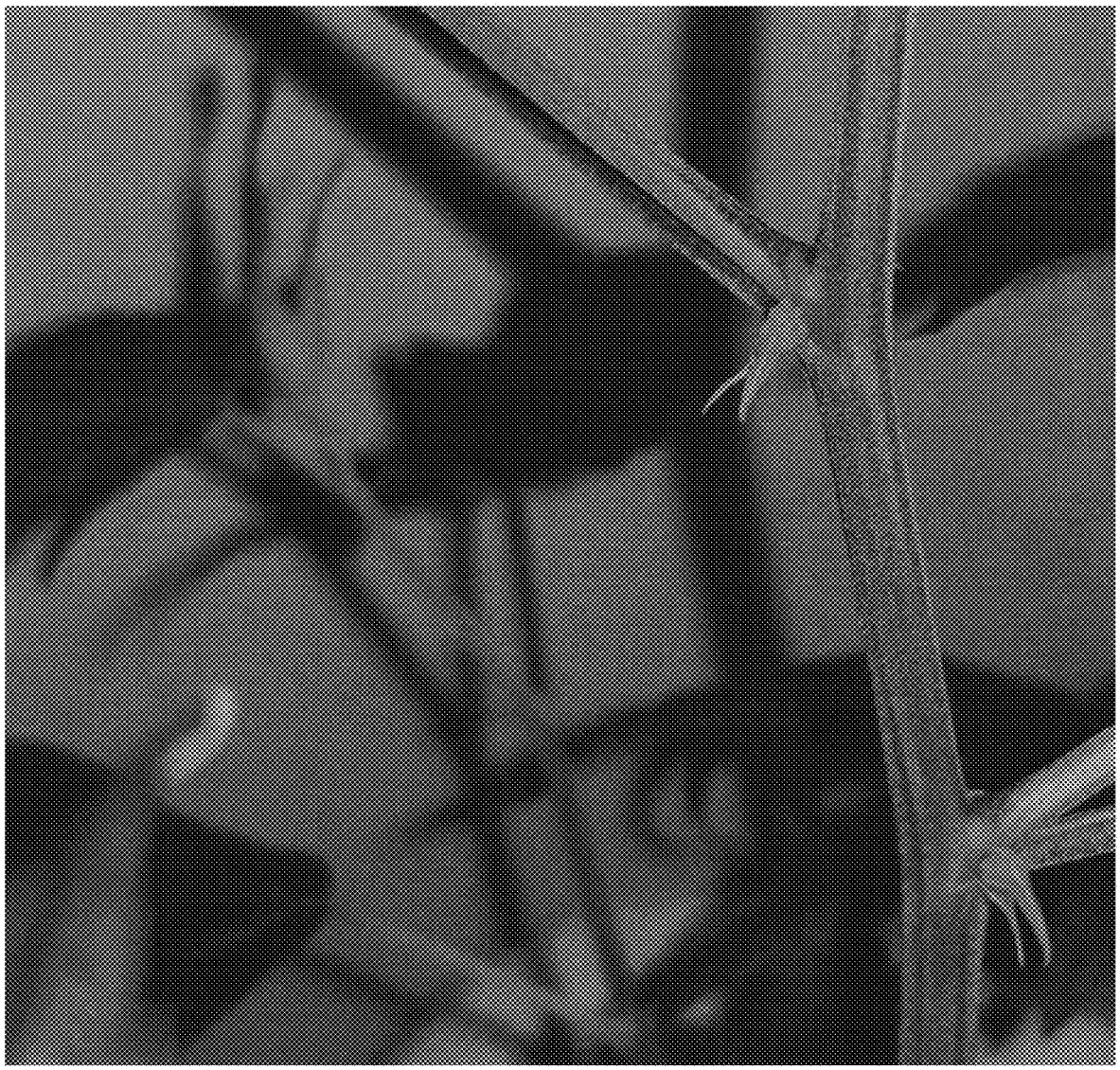
FIG. 7 shows a close-up perspective view of CC mother stem, illustrating stem shape.

| Stem | | |
|---|---|---|
| Characteristics | New Variety | Parental Variety (CC) (Female Plant) |
| Stem Shape | (See FIG. 6) Round at maturity. Immature or new growth has ridges, with a relatively pentagonal shape. Young growth is pubescent, older growth loses the hairs. Ridges are slightly furrowed, more protruding angles connected by flat sides. Nodes, where branches meet the stalk, bulge to support large flowers. Main stem internodes are long compared to other *Cannabis* cultivars. | (See FIG. 7) At maturity, round and in the bottom/trunk of the plant, growth appears woody. Immature or new growth has ridges, approximately pentagonal in shape. Between nodes, the stem angles slightly to give a zig-zag appearance. |
| Stem Diameter at Base | 2-10 cm | 3-12 cm |
| Stem Color | 144A to 146A | 144A to 146A |
| Stem Pith Type | Thick to woody | Moderate to thick |

TABLE IV

| Inflorescence | |
|---|---|
| Characteristics | New Variety |
| Flowering (blooming) habit | Dioecious. Once branching also occurs at the node, the flower will grow >1 cm up from the branch before producing a flower. Flowers grow tubular with a solid cola. |
| Proportion of female plants | Around 50% Very Stable Dioecious |
| Inflorescence Position | Above branches at nodes. Slight stem grown for bud to be above/separate from branch. |
| Flower arrangement | Overlapping, congested, individual flowers grow in tubular formation and grow separate from others. Large internodes keep buds separate, even if branching on the same node, not stacked. |
| Number of Flowers per plant | Hundreds to thousands |
| Flower shape | Asymmetrical growth. Flower itself may have bilateral symmetry. Surrounding leaves are sparse and do not fully circle the flower as with other cannabis strains. The leaves are more layered with further distance between them so they do not appear as clustered around the flower. |
| Flower (individual pistillate) length | 5-10 mm |
| Flower (compound cyme) diameter | 2-12 cm |
| Corolla | No defined corolla |
| Corolla Color (RHS number) | N/A |
| Bract shape | Small, ovate with tapering apex. Hidden under the leaves surrounding the flower, directly below each individual flower. Bracts are typically 2-3mm and are covered in glandular trichomes. |
| Bract color (RHS number) | 149B to 150A |
| Bracteole shape (general description) | Same as bract. More within the flower cluster. Hard to identify without dissection. Roughly 0.25-1 mm in size; very small. |
| Bracteole color (RHS number) | 149B to 150A |
| Calyx Shape (general description) | Triangular conical, about 1-3mm and covered in glandular trichomes |
| Calyx color (RHS number) | 143A to 143C |
| Stigma shape | Ovate shape with long tapering apex where 2 spindle-like styles protrude. |
| Stigma length | 3-10 mm |
| Stigma color (RHS number) | 149C to 149D |
| Trichome shape | Capitate stalked gland, long stalk with smaller bulb on top. In mature plants grow on flowers, petioles, leaves and veins. |
| Cystolithic non-glandular | On leaves farther from bud. Leaves grow trichomes that appear glandular when surrounding the flowers. |
| Trichome color (RHS number) | Immature: 142D<br>Mature (when ready to harvest): 172A |
| Terminal Bud shape | When flowering: More radial symmetry from leaves growing without obstruction from stem. Buds generally have similar appearance because they grow protruding from their node, rather than hugging the stem/branch which allows for more equal growth around the circumference.<br>When vegetative: the bud has spindly new growth coming out. New leaves are very skinny, almost hair-like and do not grow as straight as other cannabis plants. |
| Terminal Bud color (RHS number) | Est. N144D and 150C |
| Pedicle | Present in varying lengths depending on maturity and location of bud. Length is in the range of 0.5-4 cm and color is 144A. |
| Staminate shape | N/A |
| Sepal color (RHS number) | N/A |
| Pollen description | N/A |
| Seed description | Light brown, oval, solitary, 3-7 mm in length. Typically weigh .01-.03 g. Variation observed due to environmental conditions. |
| Marbling of seed | Minimal. |
| Petal description | N/A, Apetalous |

| Characteristics | Parental Variety (CC) (Female Plant) |
|---|---|
| Flowering (blooming) habit | Dioecious, so grows pistillate flowers at nodes. Once branching also occurs at the node, the flower will grow above the branch before producing a flower. Flowers grow very bulbous, almost spherical. Leaves surrounding the buds radiate and are more present around apical buds. |
| Proportion of female plants | 50% grown from seed, normal dioecious plant |
| Inflorescence Position | Above |
| Flower arrangement | Overlapping, congested, individual flowers grow in spherical formation. Flowers are stacked or clustered at maturity. |
| Number of Flowers per plant | Hundreds to thousands |
| Flower shape | Has mostly radial symmetry with leaves growing all around the flowers. Because of its separation from other buds, grows generally spherically. |
| Flower (individual pistillate) length | 7-13 mm |
| Flower (compound cyme) diameter | 2-13 cm |
| Corolla | No defined corolla |
| Corolla Color (RHS number) | N/A |
| Bract shape | Broad /rounded base with long, tapering apex. Longer and more prominent than offspring 'C2B'. Bracts are typically 3-4 mm and are covered in glandular trichomes. |
| Bract color (RHS number) | 150A |
| Bracteole shape (general description) | Same as bract, further enclosed in flower so hard to identify without dissection. Roughly 0.5-1 mm in size; very small. |
| Bracteole color (RHS number) | 150A |

TABLE IV-continued

| Inflorescence | |
|---|---|
| Calyx Shape (general description) | Not present |
| Calyx color (RHS number) | N/A |
| Stigma shape | Ovate shape with broad base and tapering apex with 1-2 styles protruding. Generally smaller and broader than offspring 'C2B'. |
| Stigma length | 5-8 mm |
| Stigma color (RHS number) | 150A |
| Trichome shape | Capitate stalked gland, stalk is shorter than 'C2B'. In mature plants grow on flowers and petioles. |
| Cystolithic non-glandular | Present on leaves. |
| Trichome color (RHS number) | Immature: 142D<br>Mature (when ready to harvest): 172A |
| Terminal Bud shape | When flowering: More radial symmetry from leaves growing without obstruction from stem. |
| Terminal Bud color (RHS number) | 145B to 145D |
| Pedicle | Present but shorter than the 'C2B'. Length is in the range of 0.25-2 cm and color is N144C. |
| Staminate shape | N/A |
| Sepal color (RHS number) | N/A |
| Pollen description | N/A |
| Seed description | Seeds are 2-3 mm in length. The seeds have vertical lines along the sides of the seed but only 3-5 per seed. The seed is a light brown with white lines that look like veins between some of the vertical lines. |
| Marbling of seed | There is no marbling. |
| Petal description | N/A |

TABLE V

| Other Characteristics | |
|---|---|
| Characteristics | New Variety |
| Time period and condition of flowering/blooming | Flower production is initiated when plants are taken from vegetative growth at 24-hour light and switched to 12 hours of light followed by 12 hours of dark during what would be the nocturnal period. Flowers are mature typically 75 days after flowering light cycle is initiated. flowering light cycle is initiated. |
| Proportion of hermaphrodite plants | None |
| Hardiness of plant | Is cold tolerant and grows well on several different, diverse nutrient formulas. Grows in USDA hardiness zones 4-11. |
| Breaking action | Above average, very sturdy. |
| Seed Shattering | Minimal |
| Root rate after cutting/cloning | Has exhibited 100% success at new root development after cloning, Adventitious roots appear at 10-14 days. |

TABLE V-continued

| Other Characteristics | |
|---|---|
| Total THC and CBD Content at harvest maturity<br>Total CBC content at harvest maturity | Total CBD content: 8.24%<br>Total THC content: 0.3%<br>Total CBD:THC Ratio: 25:1<br>Total CBC: 3.64%<br>(CBC = .22%<br>CBD:CBC:THC |
| Characteristics | Parental Variety (CC) (Female Plant) |
| Time period and condition of flowering/blooming | Flower production is initiated when plants are taken from vegetative growth at 24-hour light and switched to 12 hours of light followed by 12 hours of dark during what would be the nocturnal period. Flowers mature typically 75 days after the |
| Proportion of hermaphrodite plants | None |
| Hardiness of plant | Tolerant to salty soil and drought conditions. Grows in USDA hardiness zones 6-11. |
| Breaking action | Above average, very sturdy. |
| Seed Shattering | Minimal |
| Root rate after cutting/cloning | Has exhibited 100% success at new root development after cloning. Adventitious roots appear at 10-14 days. |
| Total THC and CBD Content at harvest maturity<br>Total CBC content at harvest maturity | Total CBD content: 15%<br>Total THC content: 0.5%<br>Total CBD:THC Ratio: 30:1<br>Total CBC: ND<br>and CBCA = 3.9%)<br>Ratio = 25:9:1 |

The botanical descriptions provided are generalizing from plants grown indoors in controlled conditions. Cannabinoids were measured by extracting flower samples in ethanol and running samples on a Shimadzu LC 2030 3D plus with PDA detector (HPLC/PDA) instrument calibrated with cannabinoid standards from Cerilliant Chemical. Total potential cannabinoid content is measured using a formula to account for decarboxylation of the acidic forms to allow for more accurate estimation. The formulas used are provided for convenience:

$$\text{Total THC}=\text{THC}+(\text{THCA}*(0.877));$$

$$\text{Total CBD}=\text{CBD}+(\text{CBDA}*(0.877));$$

$$\text{Total CBC}=\text{CBC}+(\text{CBCA}*(0.877)).$$

The K father, similar to 'C2B', has alternate, palmately compound leaves with 3 to 5 leaflets when immature and up to 9 at maturity. The leaflets have jagged serrate margins with the tooth apex angled towards the leaflet apex and about 19 to 29 teeth per leaflet. The leaves with the petiole are about 12 to 24 cm long and the petiole alone is about 4.2 to 8 cm long. The middle largest leaflet is about 7 to 16 cm long and 1.5 to 2 cm wide for a 4:1 or 8:1 length to width ratio. Generally, the K variety has the potential to produce 4% to 6% CBD and 0.13% to 0.27% THC which is lower than 'C2B' and K has no detectable levels of CBC. Other physical differences are present between 'C2B' and the K father due to the different appearances between male and female *Cannabis* plants. For example, males produce pollen sacs, are more-stout and taller, and have thicker stalks while females produce buds that grow into inflorescences and are usually shorter.

When compared to the CC mother, 'C2B' is generally a taller, more-slender plant. The 'C2B' grows faster with longer internodes which allows for the plant to reach taller heights but does not have as many leaves nor buds. The leaves of 'C2B' themselves even show similarities to the growth of the plant, with CC having leaflets that are much broader and with a smaller length:width ratio. The 'C2B' leaves more closely resemble the father, K, rather than the mother, CC. 'C2B' generally grows much-longer and skinnier leaflets that contribute to its sparse appearance. On the margins, 'C2B' has 28-32 serrations whereas CC has only 23-25. Although both plants grow relatively solitary, non-overlapping buds, CC is bushier and has more leaves growing radially around the buds with the apical bud fully surrounded. 'C2B' has buds that only have one or two leaves surrounding it and the apical has leaves that radiate in different layers. The distinction in density of leaves is prominent because the 'C2B' has long internodes where leaves grow which produce more space between the already-skinny leaves. At nodes where branches protrude from the stem, CC has smooth junctions (see FIG. 7), whereas 'C2B' has a bulge at the connection point (see FIG. 6).

When compared to another *Cannabis sativa* Hemp variety, CW24, the 'C2B' grows much skinnier and with less foliage. The CW24 grows flowers that are clustered and stack on top of one another near the apex of each branch. The leaves are generally radiating around each bud and grow tall and erect with no bending at maturity. 'C2B', on the other hand, grows much more sparsely, with buds grown separately and spread out by large internodes.

Growth conditions:

*Vegetative growth period.*—24 hour light continuously. 78° F. and 60% humidity.

*Flower production period.*—12 hour light followed by 12 hour dark cycle repeating. 78° F. and 45% humidity.

Outdoor growth: 'C2B' was grown outdoors on a farm located in Sonoma County, Calif. The plants were planted as 30-day clones early in the season, Aug. 16, 2019, resulting in an early flowering stage and smaller adult plants. The 'C2B' plant has the potential to reach a maximum of 15 to 17 feet tall and 10 feet wide. Compared to indoor growth, the plant will be more robust and have a faster growth rate with wider leaves. When grown outdoors, the father, K, variety will reach 10 to 15 feet tall and 10 feet wide and the mother, CC, variety will reach 8 to 10 feet tall and 6 to 8 feet wide.

Vigor: Exhibits most-vigorous and rapid growth when transitioning between vegetative and flowering growth.

Coloration: Deep bluish green with a lighter, yellowish underside. Changes in coloration occur with nutrient deficiencies or other variation in growing maintenance.

The invention claimed is:

1. A new and distinct cultivar of hemp plant, named 'C2B', as herein described and illustrated.

* * * * *